US012102318B2

(12) United States Patent
Penupolu et al.

(10) Patent No.: US 12,102,318 B2
(45) Date of Patent: Oct. 1, 2024

(54) TISSUE REPAIR DEVICE AND METHOD TO REPAIR TISSUE BY DEPLOYING IMPLANTS

(71) Applicant: Healthium Medtech Limited, Bangalore (IN)

(72) Inventors: Anoop Penupolu, Bangalore (IN); Jagadeeswaran Kasinathan, Bangalore (IN)

(73) Assignee: Healthium Medtech Limited, Bengaluru (IN)

( * ) Notice: Subject to any disclaimer, the term of this patent is extended or adjusted under 35 U.S.C. 154(b) by 270 days.

(21) Appl. No.: 17/462,238

(22) Filed: Aug. 31, 2021

(65) Prior Publication Data

US 2022/0061832 A1   Mar. 3, 2022

(51) Int. Cl.
*A61B 17/04* (2006.01)
*A61B 17/00* (2006.01)

(52) U.S. Cl.
CPC ............ *A61B 17/0401* (2013.01); *A61B 2017/00367* (2013.01); *A61B 2017/0409* (2013.01); *A61B 2017/0464* (2013.01)

(58) Field of Classification Search
CPC ........ A61B 2017/0409; A61B 17/0401; A61B 2017/0464; A61B 17/0469; A61B 2017/0417; A61B 2017/0414; A61B 2017/0496; A61B 2017/0475; A61B 17/0482; A61B 2017/0404; A61B 2017/0458; A61B 2017/0406; A61B 2017/0419; A61B 2017/0446; A61B 2017/0448; A61B 2017/0459;

(Continued)

(56) References Cited

U.S. PATENT DOCUMENTS

| | | | |
|---|---|---|---|
| 2002/0019649 A1* | 2/2002 | Sikora | A61B 17/0401 606/232 |
| 2015/0223803 A1* | 8/2015 | Trawick | A61B 17/0401 606/228 |
| 2016/0354078 A1* | 12/2016 | Overes | A61B 17/0401 |

(Continued)

FOREIGN PATENT DOCUMENTS

KR          102347660 B1 *  1/2022

OTHER PUBLICATIONS

Written Opinion for PCT/IB2021/057934 (Year: 2022).*

*Primary Examiner* — Katherine M Shi
(74) *Attorney, Agent, or Firm* — Grandhi Law Chambers; Krishna C V Grandhi

(57) ABSTRACT

Exemplary embodiments of a tissue repair device to repair tissue by deploying implants, comprising: a selector knob is configured to allow a user to change from a default position to a first position, position is indicated by a window positioned on a handle; a depth control knob is configured to adjust an exposure length of a needle under a depth control sheath to an appropriate or desired length to deploy a first implant and a second implant to secure with a tissue, a deployment knob is configured to push a pusher rod to deploy first implant from needle for delivering of a flexible member to secure tissue, deployment knob is configured to automatically spring back to a pre-specified position after deploying first implant from needle, deployment knob configured to push pusher rod to deploy second implant from needle for delivering of flexible member to secure tissue.

15 Claims, 15 Drawing Sheets

(58) Field of Classification Search
CPC ...... A61B 2017/047; A61B 2017/0474; A61B 17/0483
See application file for complete search history.

(56) References Cited

U.S. PATENT DOCUMENTS

2017/0100119 A1\* 4/2017 Baird ................. A61B 17/0469
2023/0014258 A1\* 1/2023 Lawrie ............... A61B 17/3421

\* cited by examiner

TISSUE REPAIR DEVICE AND METHOD TO REPAIR TISSUE BY DEPLOYING IMPLANTS

CROSS-REFERENCE TO RELATED APPLICATIONS

This application claims priority benefit of Indian non-provisional patent application No: 202041037534, filed on Aug. 31, 2020, entitled "Tissue Repair Device and Method to Repair Tissue by Deploying Implants". The entire contents of said patent application is hereby incorporated by reference herein.

TECHNICAL FIELD

The disclosed subject matter relates generally to surgical devices for repairing tissue, and more particularly to a tissue repair device and method to deploy implants for repairing tissue.

BACKGROUND

Surgical devices for assisting a medical practitioner in placing stitches during surgical procedures are particularly helpful and require placement of secure and accurate sutures in difficult to access regions of the body. In the human body, bone or tissue can require repair when a tear forms in the tissue include, but are not limited to, a meniscus or a soft tissue, a meniscus in a knee joint, a lateral collateral ligament in the knee, a labrum tendon in the shoulder or hip, a popliteal ligament in the leg, and the like. For example, forceful twisting or rotation of the knee (or other joint) can tear the meniscus, which can require surgical repair of the meniscus. The advent of arthroscopic techniques and endoscopic equipment have reduced the size and depth of the incision required to perform the repair procedure. However, the use of conventional devices in many cases requires a highly skilled surgeon to perform the repair, and usually requires complete immobilization of the surgical area following the repair procedure. Surgical repair of cartilage and muscle in joints such as the knee often requires extraordinary skill on the part of the surgeon to reduce damage to adjacent nerves, blood vessels, muscles and tendons in the knee joint. In particular, surgical repair of the fibrocartilage disks within the knee known as the menisci, which are attached peripherally to the joint capsule, requires precision to avoid such damage.

In the past, meniscal surgery has included procedures for partial to complete removal of a torn meniscus, as well as attempts to surgically suture, staple or tack the tear in the meniscus to allow for healing. Other techniques include removal of portions of the meniscus to arrest the spread of the tear. One method for repairing a damaged tissue involves arthroscopic surgery. The goal of surgery is to hold the damaged tissue firmly together for a length sufficient to promote healing. One example of an existing device is the FAST-FIX™ The existing device, which is designed to repair tears in soft tissue, such as the meniscus. This device for use in wound closure, is shown and described in U.S. Pat. No. 7,153,312, and also US Pat. Application No. 20170027557 discloses system and method for all-inside suture fixation for implant attachment and soft tissue repair. However, the available devices often misfire, create unpredictable situations of deployment, either over-cinch or under-cinch, create possibilities of un-predictable results.

In the light of aforementioned discussion, there exists a need for a tissue repair device and method to deploy implants for repairing tissue.

BRIEF SUMMARY

The following presents a simplified summary of the disclosure in order to provide a basic understanding to the reader. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

An objective of the present disclosure is directed towards an easier ergonomic single handed deployment of implants to avoid misfire of implants.

Another objective of the present disclosure is directed towards providing safety and secure deployment of implants.

Another objective of the present disclosure is directed towards avoiding the slippage of a second implant or last implant.

Another objective of the present disclosure is directed towards a novel device for repairing torn tissue and muscle such as the menisci in the knee joint which expedites the surgical process and facilitates healing of the tear.

Yet another objective of the present disclosure is directed towards preventing the misfire or accidental deployment of implants for safety and security.

Yet another objective of the present disclosure is directed towards generating an audible click feedback of deployment to assure a user.

Yet another objective of the present disclosure is directed towards providing knot construction for a cinching mechanism.

Yet another objective of the present disclosure is directed towards allowing a simpler and firmer repair of tissue by means of the cinching mechanism.

Exemplary embodiments of the present disclosure directed towards a tissue repair device and method to repair tissue by deploying implants.

According to an exemplary embodiment of the present disclosure, said tissue repair device comprising a handle; a depth control sheath is coupled to said handle and a needle is partially housed in said depth control sheath; one or more implants are disposed entirely within said needle.

According to another exemplary embodiment of the present disclosure, said tissue repair device comprising a selector knob is configured to allow a user to change a default position to a first position, said selector knob is configured to avoid misfire of said first implant in said default position, whereby said position is indicated by a window positioned on said handle.

According to another exemplary embodiment of the present disclosure, said tissue repair device comprising a depth control knob is configured to adjust an exposure length of said needle under said depth control sheath to at least one of: a maximum length; and a minimum length to deploy said first implant and said second implant or series of implants to secure with a tissue.

According to another exemplary embodiment of the present disclosure, said tissue repair device comprising a deployment knob is configured to push a pusher rod to deploy said first implant from said needle after changing said selector knob from said default position to said first position for delivering a flexible member to secure said tissue, said deployment knob is configured to automatically spring back to a pre-specified position after deploying said first implant from said needle, said selector knob is configured to avoid misfire of said first implant in said default position, said deployment knob configured to push said pusher rod to deploy said second implant from said needle after changing said selector knob from said first position to a second position for delivering said flexible member to secure said tissue, said selector knob is configured to avoid misfire of said second implant or series of implants in said first position.

BRIEF DESCRIPTION OF DRAWINGS

Other objects and advantages of the present invention will become apparent to those skilled in the art upon reading the following detailed description of the preferred embodiments, in conjunction with the accompanying drawings, wherein like reference numerals have been used to designate like elements, and wherein.

DETAILED DESCRIPTION

Figure 1A:
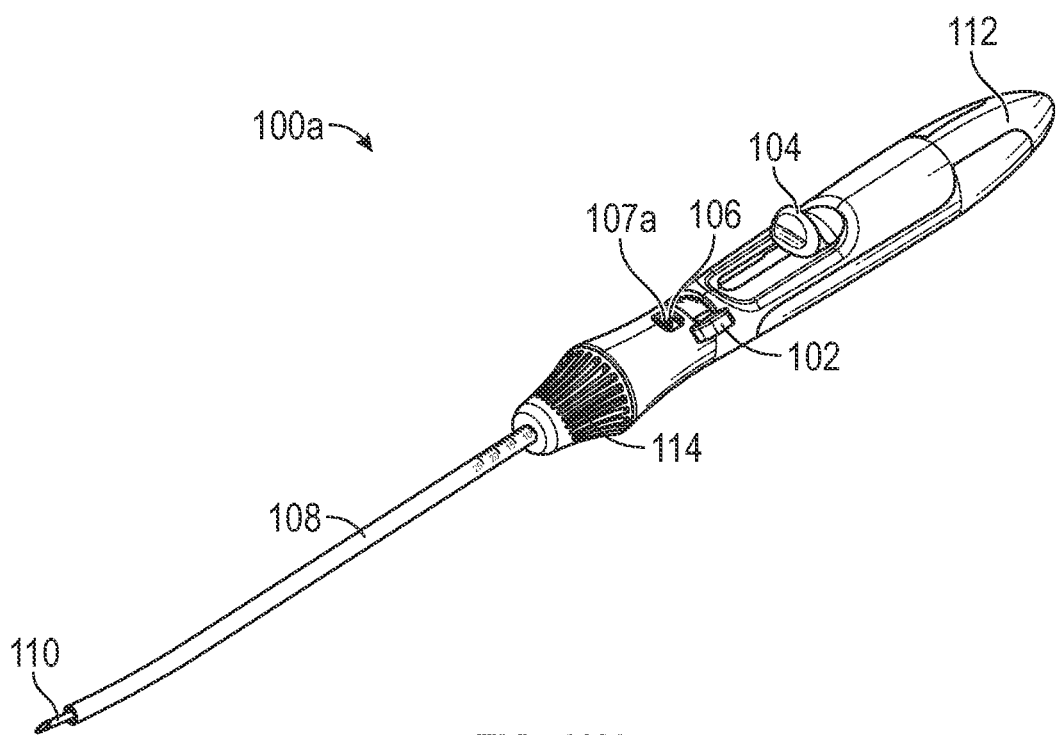
FIG. 1A, FIG. 1B are diagrams depicting a tissue repair device to repair a tissue of a knee by deploying implants, in accordance with one or more exemplary embodiments.

It is to be understood that the present disclosure is not limited in its application to the details of construction and the arrangement of components set forth in the following description or illustrated in the drawings. The present disclosure is capable of other embodiments and of being practiced or of being carried out in various ways. Also, it is to be understood that the phraseology and terminology used herein is for the purpose of description and should not be regarded as limiting.

The use of "including", "comprising" or "having" and variations thereof herein is meant to encompass the items listed thereafter and equivalents thereof as well as additional items. The terms "a" and "an" herein do not denote a limitation of quantity, but rather denote the presence of at least one of the referenced item. Further, the use of terms "first", "second", and "third", and the like, herein do not denote any order, quantity, or importance, but rather are used to distinguish one element from another.

Figure 1B:
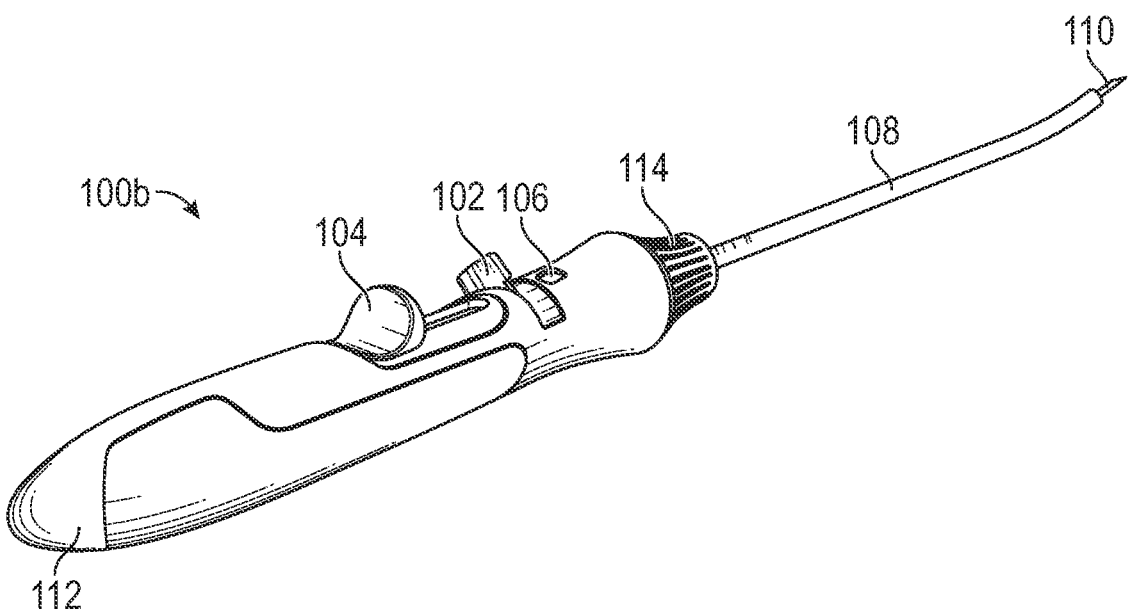

The tissue repair device referred to herein in this disclosure refers to a device that may be used to repairing a meniscus or soft tissue and the like. FIGS. 1B, FIG. 1A, FIG. 1B are diagrams 100a, 100b depicting a tissue repair device to repair a tissue of a knee by deploying implants, in accordance with one or more exemplary embodiments. The tissue repair device 100a and 100b includes a selector knob 102, a deployment knob 104, a window 106, a depth control sheath 108, a needle 110, a handle 112, and a depth control knob 114. The first implant and the second implant (shown in FIG. 1C, FIG. 1D) may be disposed entirely within the needle 110. The window 106 may be configured to indicate the position of deployment adjusted by the selector knob 102. The position of deployment adjusted by the selector knob 102 may include, but not limited to, a default position '0' 107a, a first position '1' 107b, and a second position '2' 107c (shown in FIG. 2C), a third position '3' (For example, 107d), and so forth.

Figure 1C:
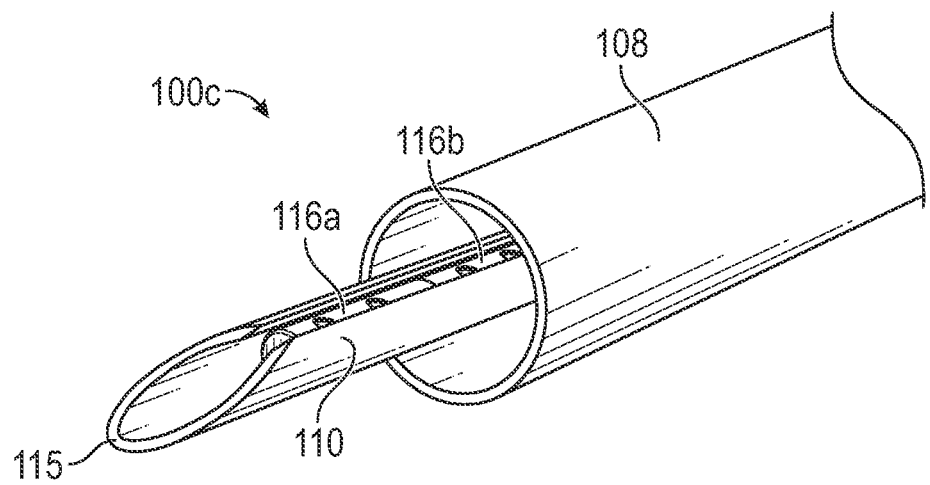
FIG. 1C, FIG. 1D are diagrams depicting a perspective view of the needle tip and implants close-up of the tissue repair device, in accordance with one or more exemplary embodiments.
Figure 1D:
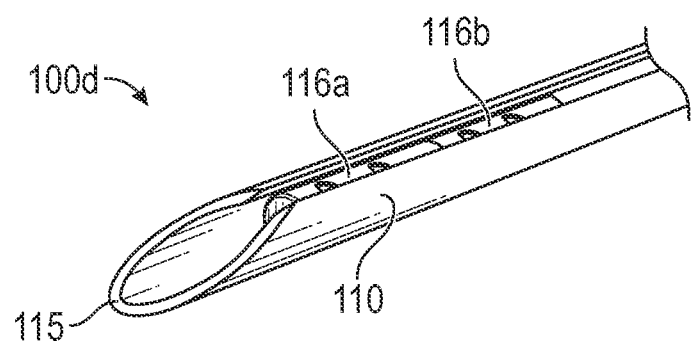
Figure 1E:
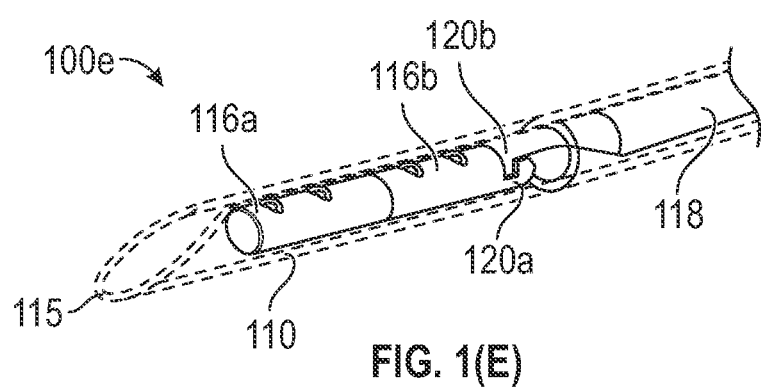
FIG. 1E is a diagram depicting a transparent view of the depth control sheath 108 of the tissue repair device, in accordance with one or more exemplary embodiments.
Figure 1O:
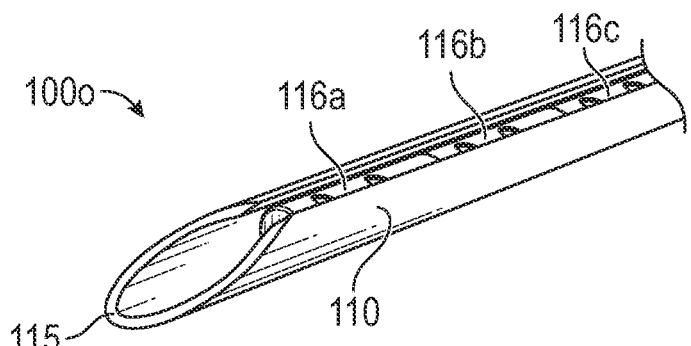
FIG. 1O is another example diagram depicting the implants of the tissue repair device, in accordance with one or more exemplary embodiments.
Figure 2A:
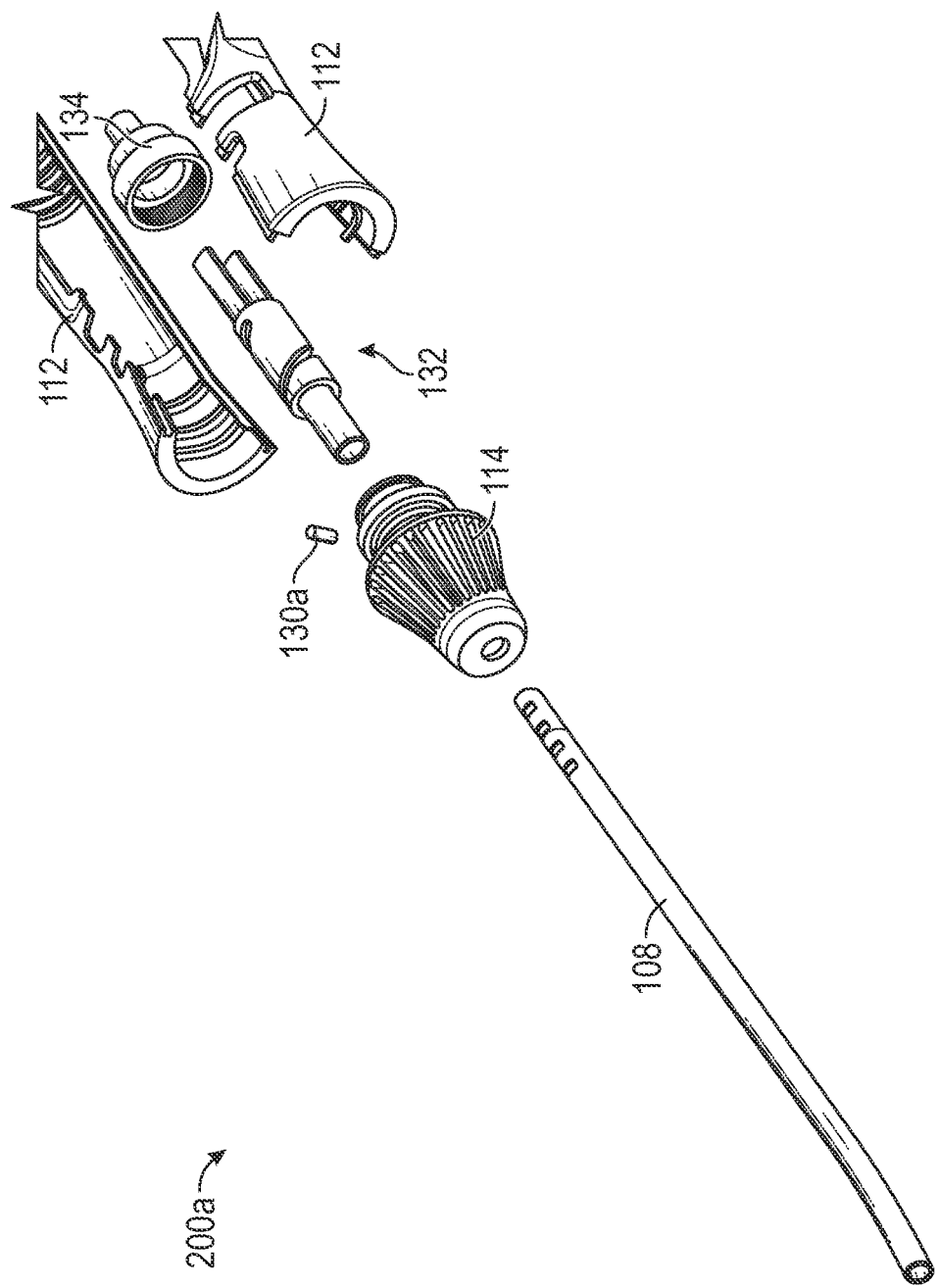
FIG. 2A is a diagram depicting an exploded view of the tissue repair device, in accordance with one or more exemplary embodiments.
Figure 2B:
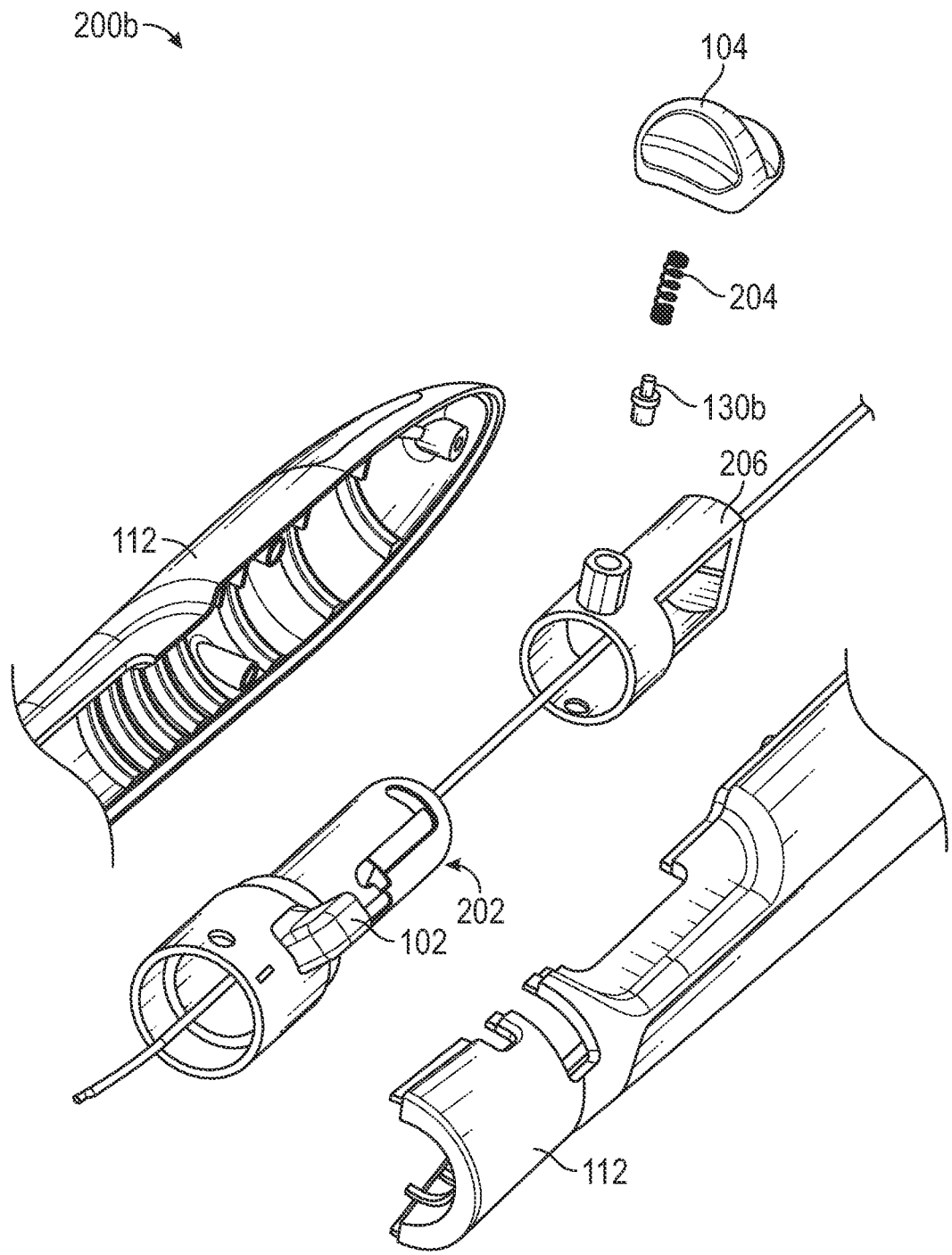
FIG. 2B, FIG. 2C are diagrams depicting the exploded view of the handle and the default configuration of the tissue device, in accordance with one or more exemplary embodiments.
Figure 2C:
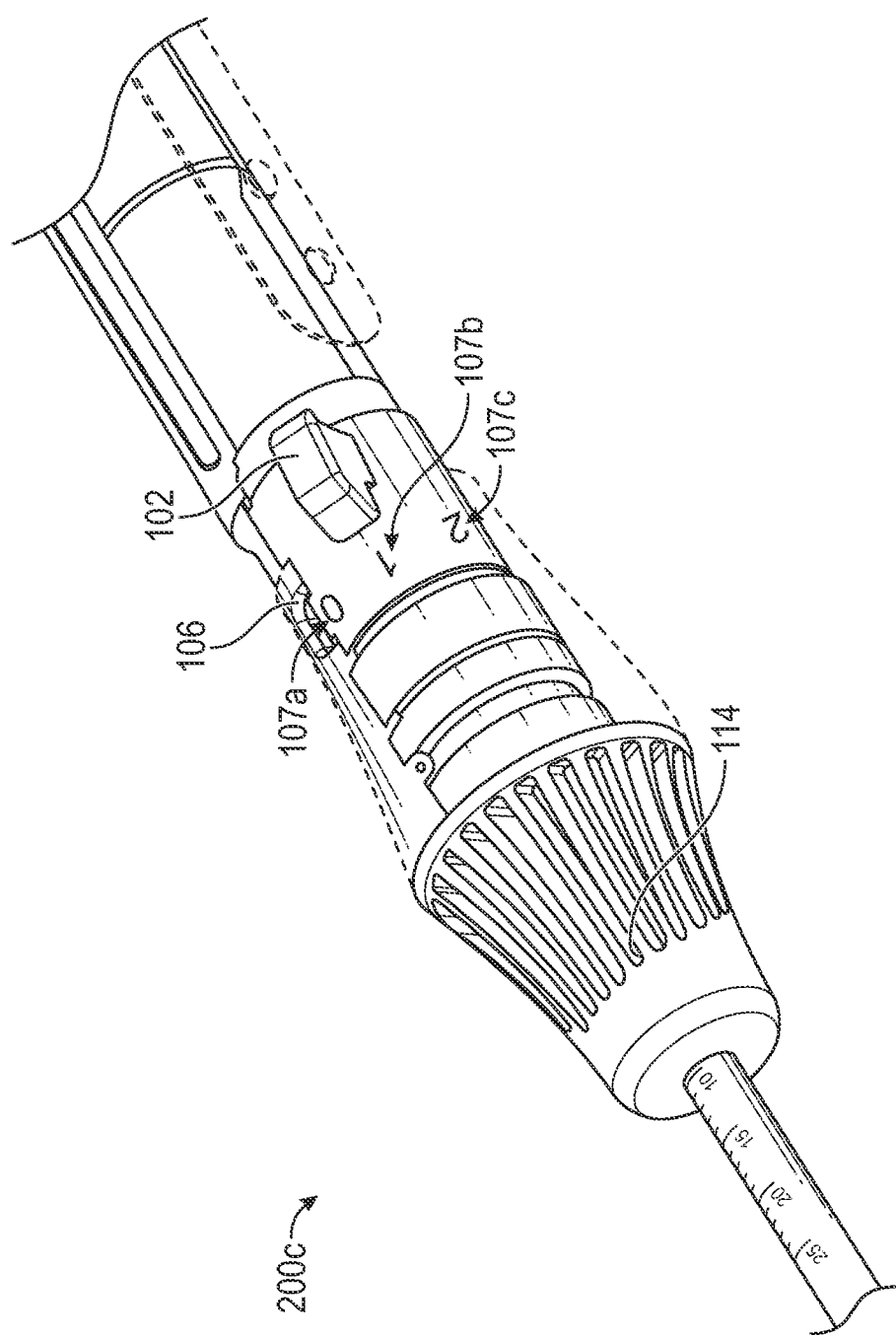

The selector knob 102 may be configured to allow a user to change from the default position 107a to the first position 107b (shown in FIG. 2C). The user may include, but not limited to, a medical practitioner, a doctor, a physician, a surgeon, a specialist, and so forth. The deployment knob 104 may be configured to generate an audible click confirmation while changing the position of the deployment of the selector knob 102. The deployment knob 104 may also be configured to allow the user to push a pusher rod (shown in FIG. 1E) by a specified distance to deploy the first implant/the second implant/the third implant (shown in FIG. 1C, FIG. 1D, FIG. 1O) after changing position of the selector knob 102 from the default position 107a to the first position 107b (shown in FIG. 2C)/the first position 107b to the second position 107c (shown in FIG. 2C)/the second position 107c to the third position for delivering of the flexible member to secure the tissue. The selector knob 102 may be configured to avoid misfire of the first implant 116a (shown in FIG. 1C, FIG. 1D) in the default position 107a/misfire of the second implant 116b (shown in FIG. 1C, FIG. 1D) in the first position 107b/misfire of the third implant 116c (shown in FIG. 1O) in the second position 107c. The deployment knob 104 may also be configured to generate the audible click confirmation while deploying the first implant/the second implant or series of implants (shown in FIG. 1C, FIG. 1D) from the needle 110.

The deployment knob 104 may be configured to automatically spring back to its pre-specified position. The deployment knob 104 may be locked when the selector knob 102 is positioned at the default position '0' 107*a*. The selector knob 102 may be configured to allow the user to change the position of deployment from the default position '0' 107*a* to the first position '1' 107*b* ((shown in FIG. 2C) to deploy the first implant (shown in FIG. 1C, FIG. 1D). The selector knob 102 may also be configured to allow the user to change the position of deployment from the first position '1' 107*b* to the second position '2' 107*c* only after the deployment of the first implant (shown in FIG. 1C, FIG. 1D). The depth control knob 114 may be configured to adjust the length of the needle 110 situated outside of the depth control sheath 108 by rotating in a clockwise or a counter-clockwise direction. The length of the needle 110 may be increased by rotating the depth control knob 114 in the clockwise direction. The length of the needle 110 may be decreased by rotating the depth control knob 110 in the counter-clockwise direction by adjusting the depth control sheath 108 covering the needle 110.

FIG. 1C, FIG. 1D are diagrams 100*c* and 100*d* depicting a perspective view of the needle tip and implants close-up of the tissue repair device, in accordance with one or more exemplary embodiments. The perspective view of the needle tip and implants close-up of the tissue repair device 100*c* includes the first implant 116*a*, the second implant 116*b*, the needle 110 and the depth control sheath 108. The perspective view of the needle tip 115 and implants close-up of the tissue repair device 100*d* includes the first implant 116*a*, the second implant 116*b*, and the needle 110. The first implant 116*a* and the second implant 116*b* may be kept in series. The needle 110 may be housed within the depth control sheath 108. The first implant 116*a* may be at proximal end of the needle tip 115. The second implant 116*b* may be behind the first implant 116*a*.

FIG. 1E is a diagram 100*e* depicting a transparent view of the depth control sheath 108 of the tissue repair device, in accordance with one or more exemplary embodiments. The transparent view of the depth control sheath 108 of the tissue repair device 100*e* includes a pusher rod 118, the first implant 116*a*, the second implant 116*b*, the needle 110, a first notch 120*a* of the second implant 116*b*, and a second notch 120*b* of the pusher rod 118. The pusher rod 118 may be configured to deploy the first implant 116*a* and the second implant 116*b* from the needle 110 by means of the deployment knob 104 (shown in FIGS. 1A, FIG. 1B). The first implant 116*a* may be positioned at the proximal end of the needle tip 115. The second implant 116*b* may be positioned behind the first implant 116*a*. The first notch 120*a* of the second or last implant 116*b* may be configured to hold the second notch 120*b* of the pusher rod 118. The second notch 120*b* of the pusher rod 118 may be configured to engage with the second or last implant 116*b* to prevent slippage or accidental deployment of this implant while deploying the previous implant 116*a*.

Figure 1F:
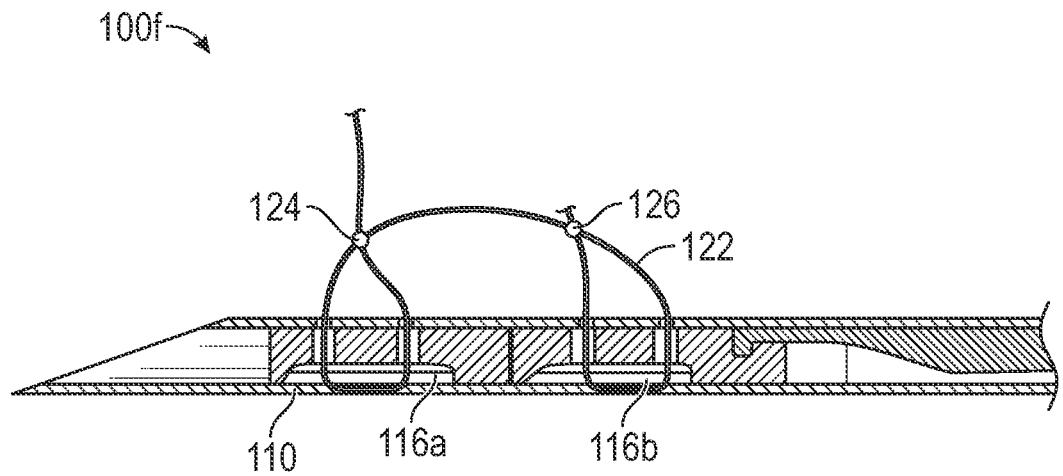
FIG. 1F is a diagram depicting a suture routing of the tissue repair device, in accordance with one or more exemplary embodiments.

FIG. 1F is a diagram 100*f* depicting a suture routing of the tissue repair device, in accordance with one or more exemplary embodiments. The suture routing of the tissue repair device 100*f* includes a flexible member 122, a first sliding knot 124, a second sliding knot 126, the first implant 116*a*, and the second implant 116*b*. The first implant 116*a* and the second implant 116*b* may be coupled via the flexible member 122 such as a suture that includes the first sliding knot 124 and the second sliding knot 126. The suture 122 may be coupled to the first implant 116*a* and the second implant 116*b*. The second sliding knot 126 may be located between the first implant 116*a* and the second implant 116*b*. A free end extends from the first sliding knot 124 and the second sliding knot 126 and the suture 122 length between the implants 116*a*, 116*b* may be reduced upon pulling the free end in one direction.

Figure 1G:
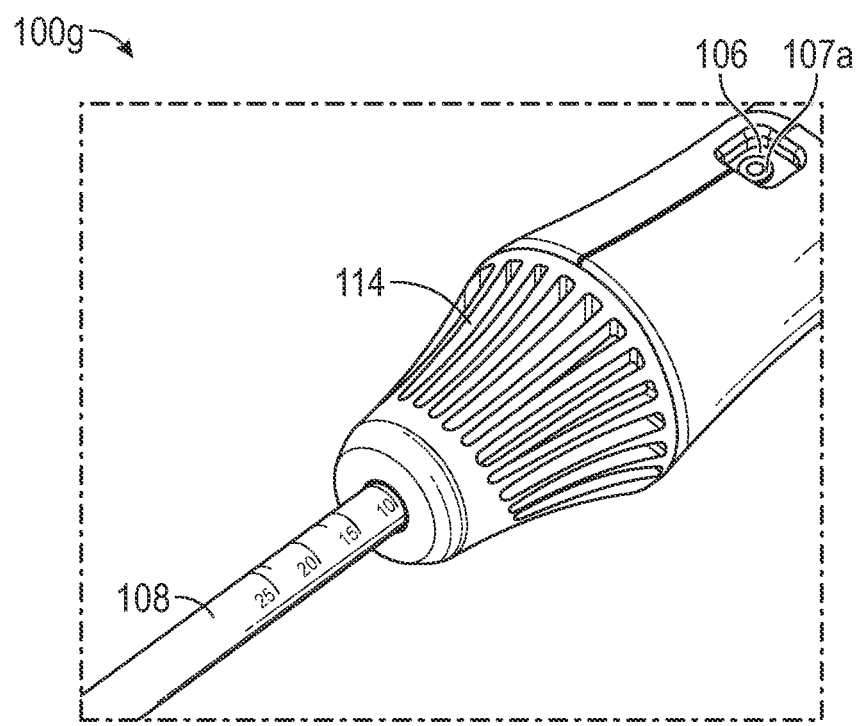
FIG. 1G is a diagram depicting a perspective view of the depth control knob of the tissue repair device, in accordance with one or more exemplary embodiments.

FIG. 1G is a diagram 100*g* depicting a perspective view of the depth control knob of the tissue repair device, in accordance with one or more exemplary embodiments.

The perspective view of the depth control knob of the tissue repair device 100*g* includes the depth control knob 114, and the depth control sheath 108. The depth control knob 114 may be configured to adjust the exposure length of the needle 110 situated under the depth control sheath 108. The exposure length of the needle 110 under the depth control sheath 108 may be adjusted to a maximum length and a minimum length by means of the depth control knob 114. The maximum exposed needle length may be 25 mm and minimum exposed needle length may be 10 mm.

Figure 1H:
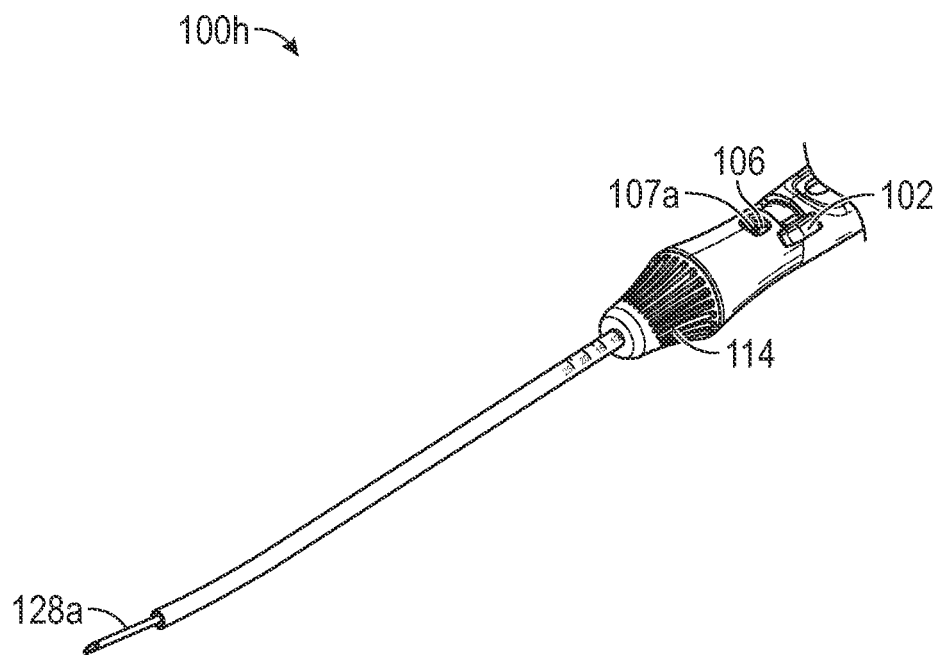
FIG. 1H, FIG. 1I are diagrams depicting the maximum and minimum exposed needle length of the tissue repair device, in accordance with one or more exemplary embodiments.
Figure 1I:
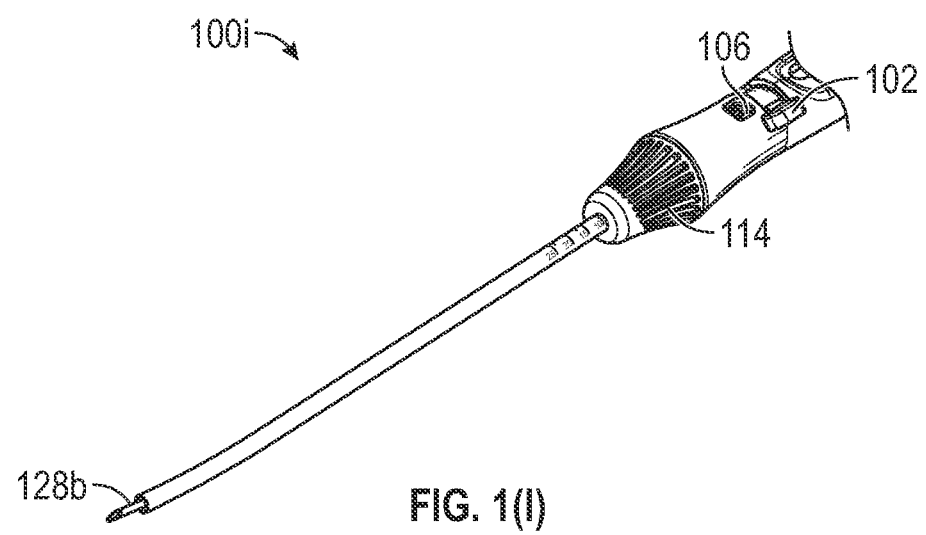

FIG. 1H, FIG. 1I are diagrams 100*h*, 100*i* depicting the maximum and minimum exposed needle length of the tissue repair device, in accordance with one or more exemplary embodiments. The maximum and minimum exposed needle length of the tissue repair device 100*h*, 100*i* includes a maximum exposed needle length 128*a* and a minimum exposed needle length 128*b*. The depth control sheath 108 may be adjusted to maximize the exposure length 128*a* of the needle 110 by rotating the depth control knob 114 in the clockwise direction. The depth control sheath 108 may be adjusted to minimize the exposure length 128*b* of the needle 110 by rotating the depth control knob 114 in the counter-clockwise direction by adjusting the depth control sheath 108 covering the needle 110.

Figure 1J:
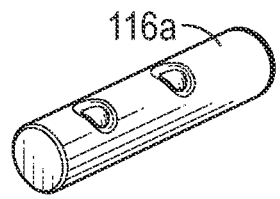
FIG. 1J, FIG. 1K, FIG. 1L are diagrams depicting the implants of the tissue repair device, in accordance with one or more exemplary embodiments.
Figure 1K:
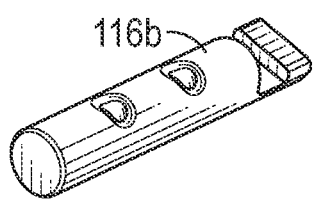
Figure 1L:
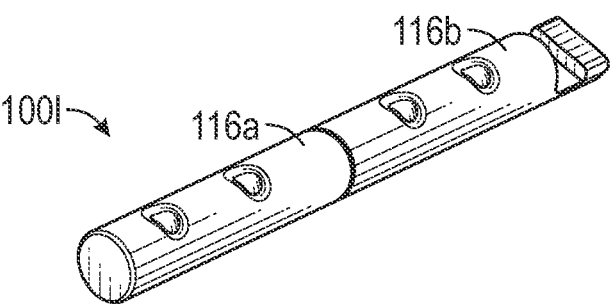

FIG. 1J, FIG. 1K, FIG. 1L are diagrams 100*j*, 100*k*, 100*l* depicting the implants of the tissue repair device, in accordance with one or more exemplary embodiments. The implants of the tissue repair device 100*j*, 100*k*, 100*l* includes the first implant 116*a*, the second implant 116*b*. The first implant 116*a* and the second implant 116*b* may be positioned in series. The first implant 116*a* and the second implant 116*b* may be coupled via the suture 122 (shown in FIG. 1F).

Figure 1M:
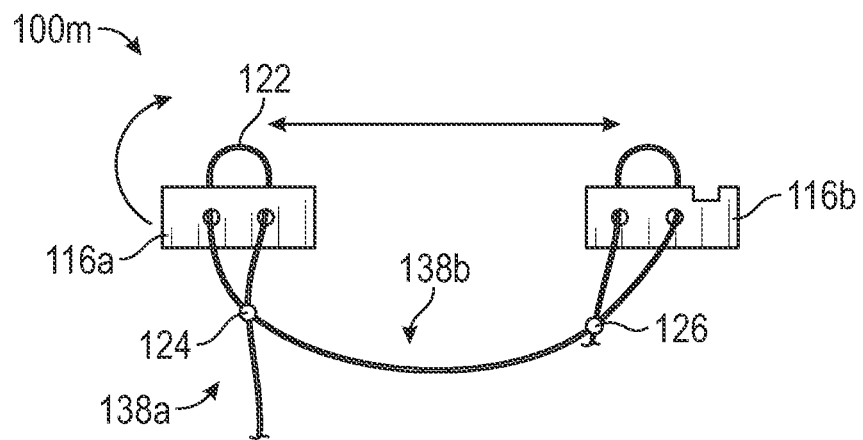
FIG. 1M, FIG. 1N are diagrams depicting the cinching mechanism and knot mechanism, in accordance with one or more exemplary embodiments.
Figure 1N:
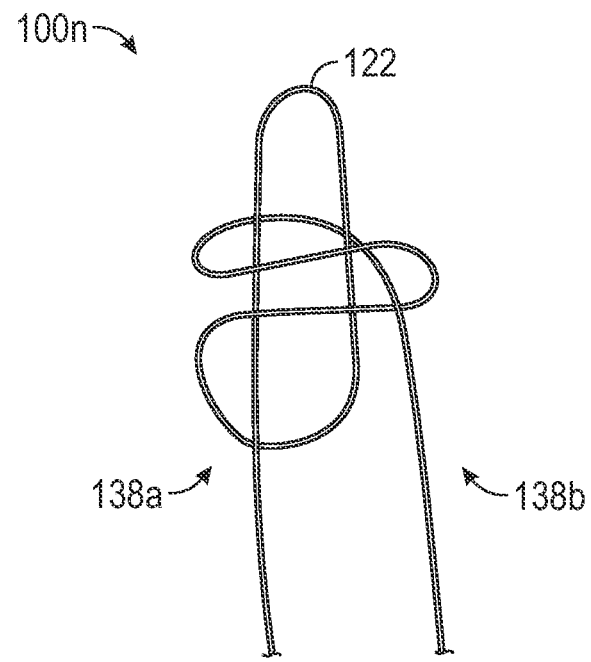

FIG. 1M, FIG. 1N are diagrams 100*m*, 100*n* depicting a cinching mechanism and a knotting mechanism, in accordance with one or more exemplary embodiments. The cinching mechanism and the knot mechanism 100*m*, 100*n* includes a pulling side 138*a*, a sliding side 138*b*, the first implant 116*a*, the second implant 116*b*, the suture 122, the first sliding knot 124, and the second sliding knot 126. The major cinching and sliding may be occurred at the first sliding knot 124. The first implant 116*a* and the second implant 116*b* may be coupled via the suture 122 that includes the first sliding knot 124, and the second sliding knot 126. The suture 122 may be coupled to the first implant 116*a* and the second implant 116*b*. The second sliding knot 126 may be located between the first implant 116*a* and the second implant 116*b*. The pulling side 138*a* may also be referred as a free end. The pulling side 138*a* extends from the first sliding knot 124 of the sliding side 138*b* and the second sliding knot 126 and the suture 122 length between the implants 116*a*, 116*b* may be reduced upon pulling the pulling side 138*a* in one direction. The knotting mechanism 100*n* includes large number of fixed knots and sliding knots.

FIG. 1O is another example diagram 100*o* depicting the implants of the tissue repair device, in accordance with one or more exemplary embodiments. The implants of the tissue repair device 100o includes the first implant 116a, the second implant 116b, the third implant 116c, and the needle 110. The first implant 116a, the second implant 116b, and the third implant 116c may be kept in series. The needle 110 may be housed within the depth control sheath 108. The first implant 116a may be at proximal end of the needle tip 115. Although the first implant 116a and the second implant 116b, is shown in FIG. 1C, an embodiment of the system 100c may support any number of implants. In an embodiment with three implants, there may be four positions such as position default position '0' 107a, a first position '1' 107b, and a second position '2' 107c (shown in FIG. 2C), a third position '3', and a fourth position '4'. In an embodiment with 'n' implants, there may be 'n' positions, and so forth.

FIG. 2A is a diagram 200a depicting an exploded view of the tissue repair device, in accordance with one or more exemplary embodiments. The exploded view of the tissue repair device 200a includes the depth control sheath 108, the needle 110, the handle casing 112, the depth control knob 114, a first pin 130a, a barrel cam 132, and a needle hub 134. The first pin 130a may be fixed in the depth control knob 114 and is locked inside a helical slot of the barrel cam 132. The depth control sheath 108 may be attached to the barrel cam 132 via the depth control knob 114. The pin 130a may be configured to force the barrel cam 132 to slide in backward direction when the depth control knob 114 is rotated in the clockwise direction thereby the length of the exposed needle 110 under the depth control sheath 108 may reach the maximum length of 25 mm. The pin 130a may be configured to force the barrel cam 132 to slide in forward direction when the depth control knob 114 is rotated in the counter-clockwise direction thereby the length of the exposed needle 110 under the depth control sheath 108 may reach the minimum length of 10 mm. The handle casing 112 may be configured to enclose the first pin 130a, the barrel cam 132, and the needle hub 134.

FIG. 2B, FIG. 2C are diagrams 200b, 200c depicting the exploded view of the handle and the default configuration of the tissue repair device, in accordance with one or more exemplary embodiments. The exploded view of the handle and the default configuration of the tissue repair device 200b, 200c include a stepped barrel groove 202, a spring 204, a pusher rod body 206, the selector knob 102 a second pin 130b, the default position 107a, the first position 107b, and the second position 107c. The spring 204 may be loaded with the second pin 130b and is trapped inside the stepped barrel groove 202 in the selector knob 102. The selector knob 102 may be configured to avoid misfire of the first implant 116a in the default position 107a/misfire of the second implant 116b in the first position 107b/misfire of the third implant 116c in the second position 107c. The pusher rod body 206 may be configured to enclose the pusher rod 118.

Figure 3A:
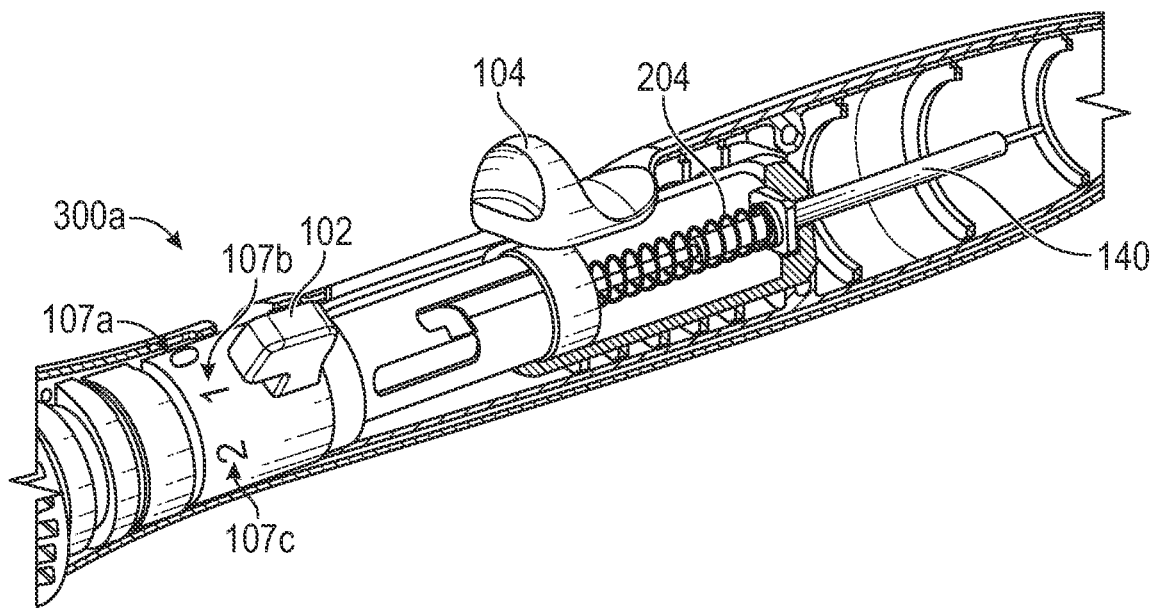
FIG. 3A FIG. 3B are diagrams depicting a default configuration of the tissue repair device, in accordance with one or more exemplary embodiments.
Figure 3B:
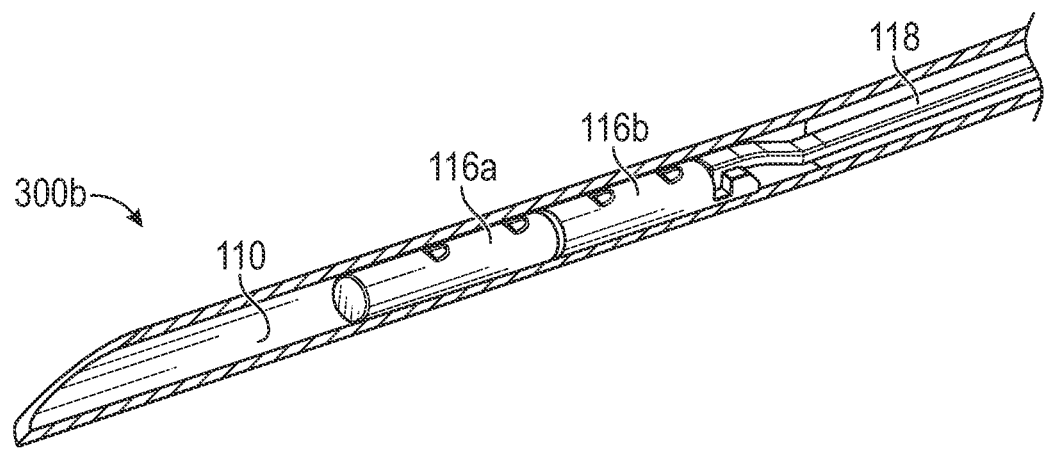
Figure 4A:
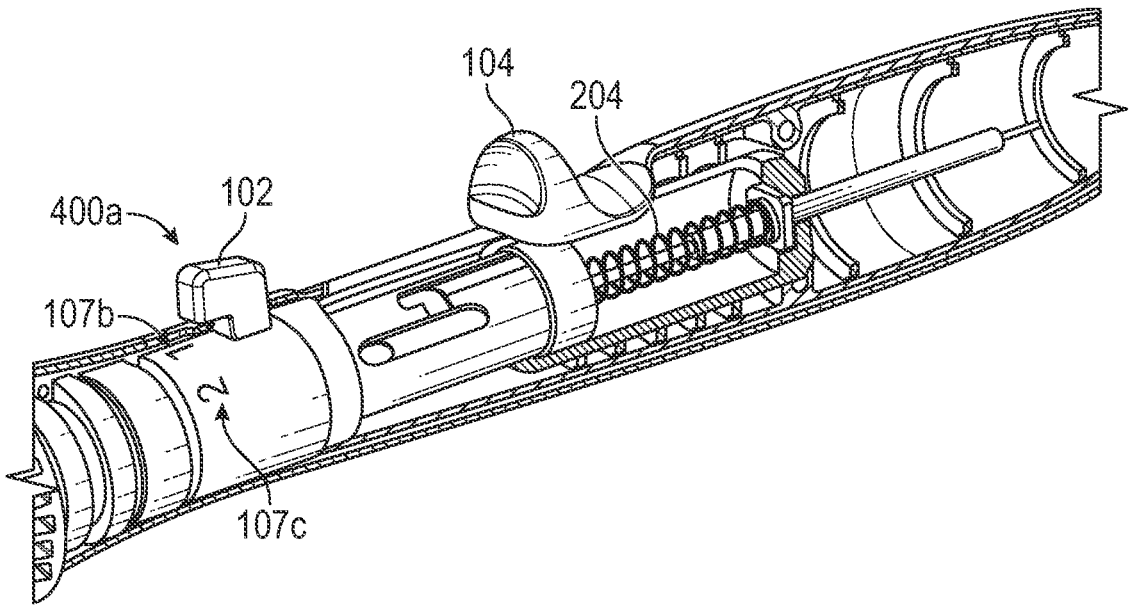
FIG. 4A FIG. 4B, FIG. 4C, FIG. 4D and FIG. 4E are diagrams depicting an activation of tissue repair device for first implant deployment, in accordance with one or more exemplary embodiments.
Figure 4B:
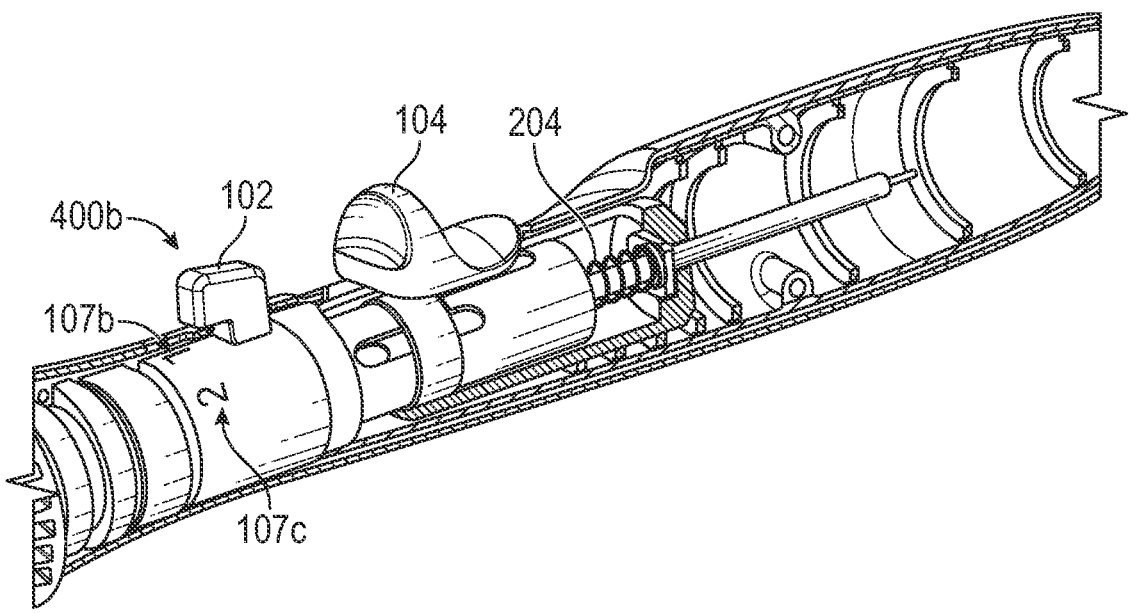
Figure 4C:
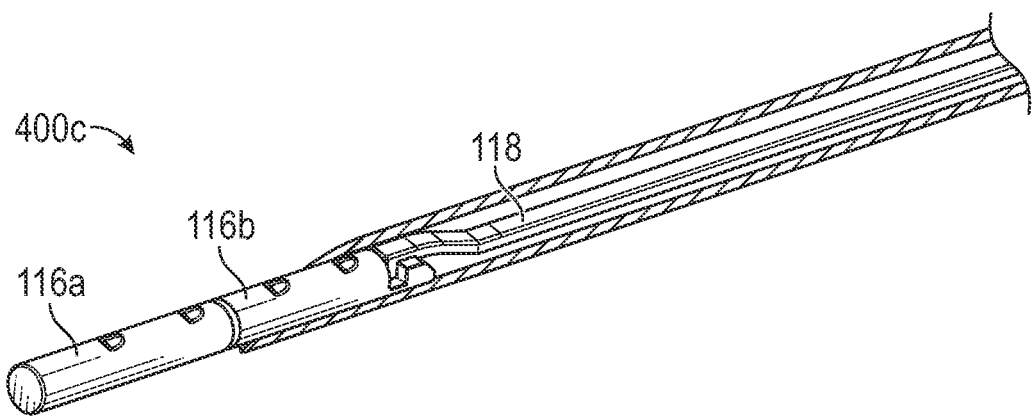
Figure 4D:
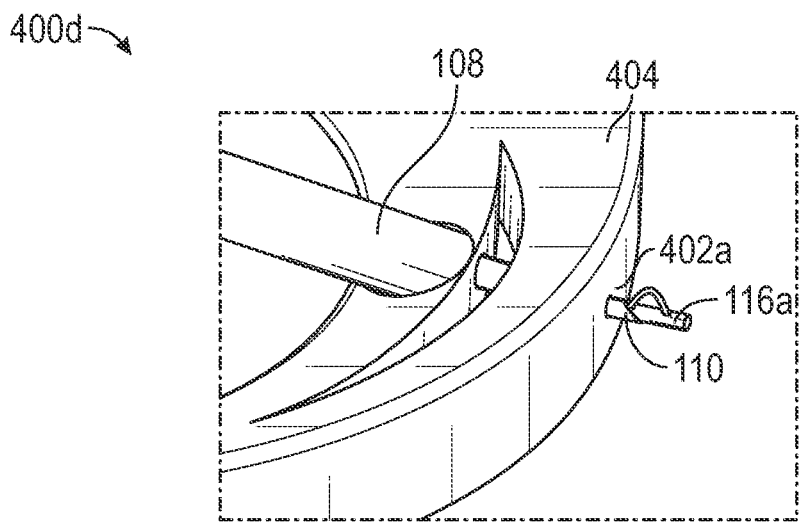
Figure 4E:
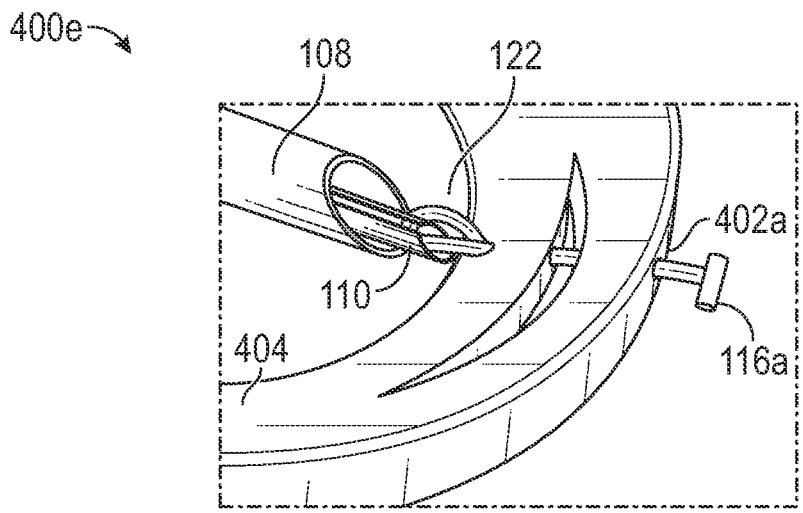

FIG. 3A FIG. 3B are diagrams 300a, 300b depicting a default configuration of the tissue repair device, in accordance with one or more exemplary embodiments. The default configuration of the tissue repair device 300a, 300b includes the selector knob 102, the needle 110, the first implant 116a, the second implant 116b, and a pusher rod insert 140. The first implant 116a, and the second implant 116b may be situated in a home position when the selector knob 102 is positioned in the default/idle position '0' 107a. The tissue repair device may be locked and may not be able to deploy the first implant 116a, and the second implant 116b when the selector knob 102 is positioned in the default position '0' 107a. The pusher rod insert 140 may be configured to integrate the pusher rod 118 with the pusher rod body 206, while pushing the deployment knob 104, pusher rod 118 may move forward.

FIG. 4A, FIG. 4B, FIG. 4C, FIG. 4D and FIG. 4E are diagrams 400a, 400b, 400c, 400d, and 400e depicting an activation of tissue repair device for first implant deployment, in accordance with one or more exemplary embodiments. The activation of tissue repair device for first implant deployment 400a, 400b, 400c, 400d, and 400e includes the selector knob 102, the deployment knob 104, the needle 110, the suture 122, the first implant 116a, the second implant 116b, a first implant site 402a, a second implant site 402b, a tissue 404, the first position 107b, and the second position 107c. The selector knob 102 may be configured to avoid misfire of the second implant 116b in the first position 107b.

Figure 5A:
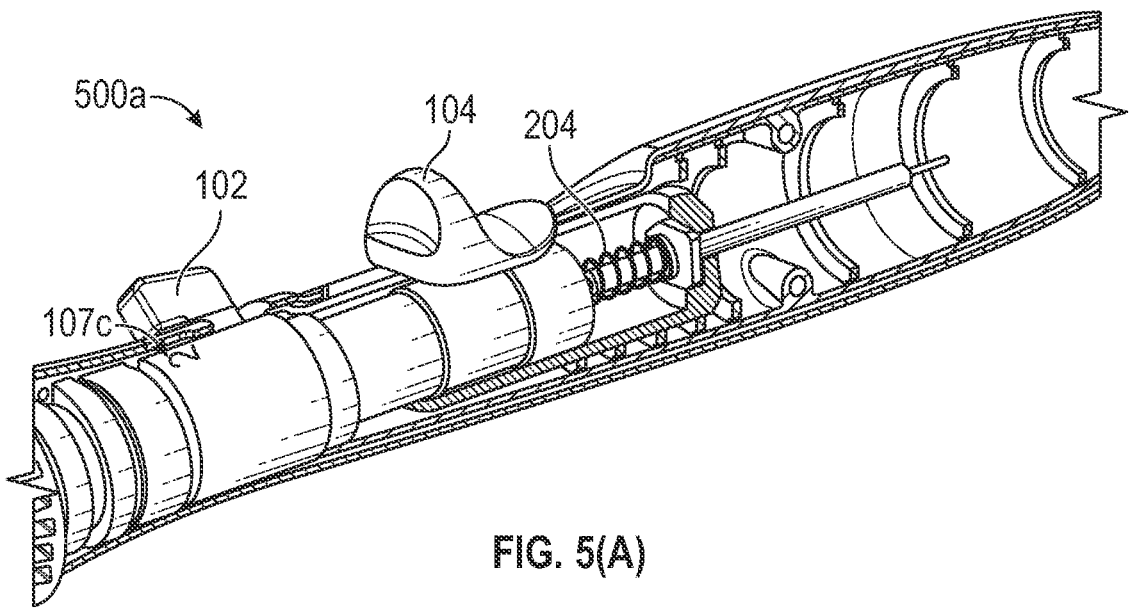
FIG. 5A FIG. 5B, FIG. 5C, and FIG. 5D are diagrams depicting an activation of tissue repair device for second implant deployment or series of implants, in accordance with one or more exemplary embodiments.
Figure 5B:
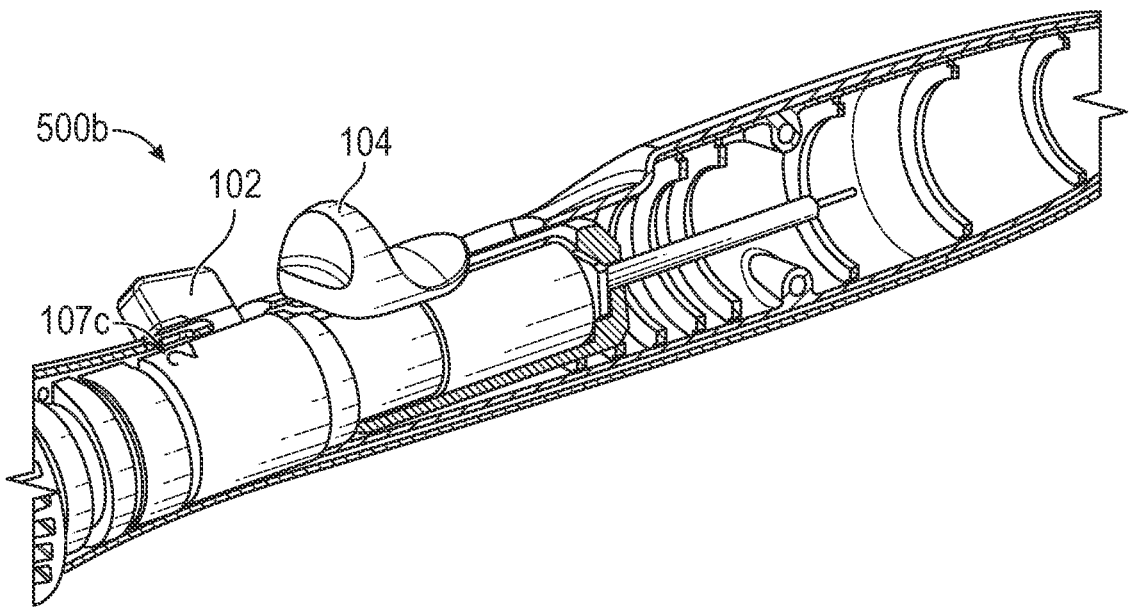
Figure 5C:
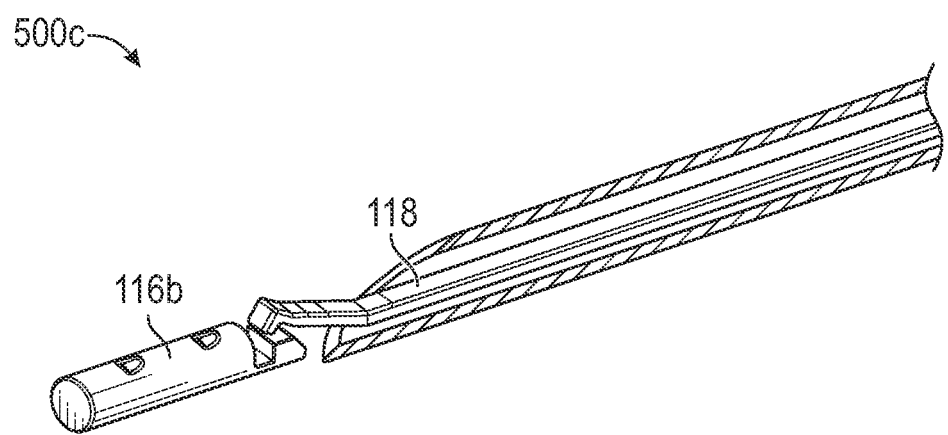
Figure 5D:
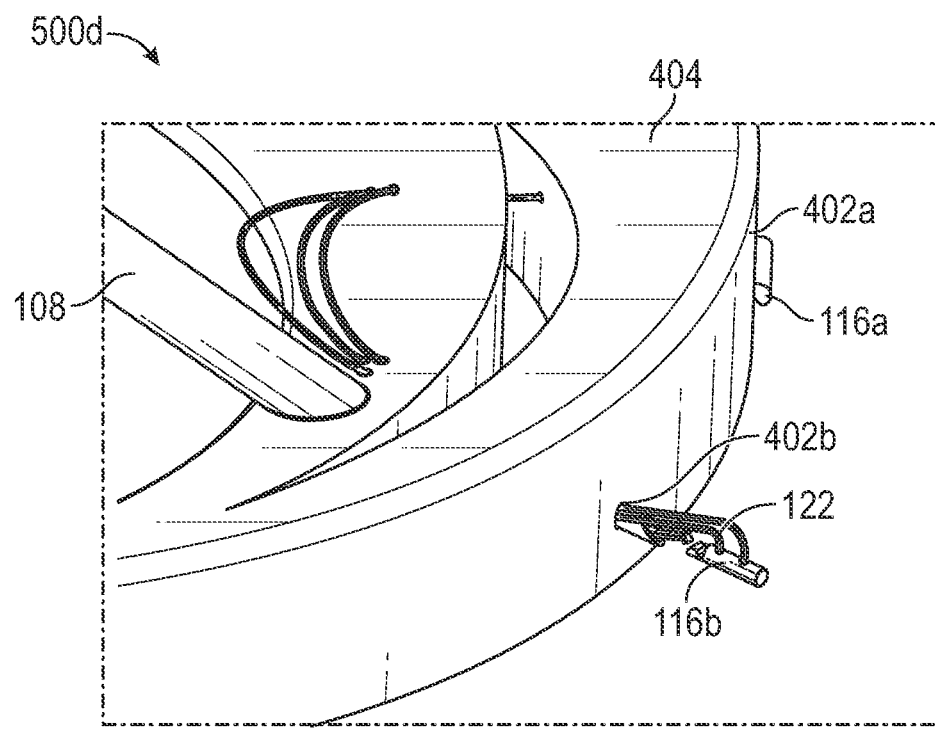

The needle 110 may pierce at a first implant site 402a then the selector knob 102 may be positioned in the first position '1' 107b. The selector knob 102 may be configured to enable the user to push the deployment knob 104 up to certain extent to deploy the first implant 116a from the needle 110 thereby retracting the needle 110 from the first implant site 402a to pierce the needle 110 to a second implant site 402b (as shown in FIG. 5D). Before deployment of the first implant 116a, the spring 204 is in an idle position. However, after deployment of the first implant 116a, the spring 204 is compressed in the deployment knob 104.

FIG. 5A FIG. 5B, FIG. 5C, and FIG. 5D are diagrams 500a, 500b, 500c, and 500d depicting an activation of tissue repair device for second implant deployment or series of implants, in accordance with one or more exemplary embodiments. The activation of tissue repair device for second implant deployment 500a, 500b, 500c, and 500d includes the selector knob 102, the deployment knob 104, the second implant 116b, the second implant site 402b, and the second position 107c. The selector knob 102 may be configured to avoid misfire of the third implant 116c in the second position 107c.

The second implant 116b may be automatically adjusted to a second home position. The needle 110 may pierce at the second implant site 402b then the selector knob 102 may be positioned in the second position '2 107c. The selector knob 102 may be configured to enable the user to push the deployment knob 104 up to extreme to deploy the second implant 116b from the needle 110. The needle 110 may be retracted from the second implant site 402b after deploying the second implant 116b. Before deployment of the second implant 116b, the spring 204 is in an idle position. However, after deployment of the first second implant 116b, the spring 204 is compressed in the deployment knob 104.

Once the second implant 116b has been deployed, the needle 110 is removed from the tissue 404 (meniscus). The tissue repair device is subsequently removed from the knee joint and the free end of the suture 122 is pulled in one direction. The sliding knot 126 may allow the suture 122 to slide towards the tissue 404, but does not allow the suture 122 to slide in the opposite direction.

Figure 6:
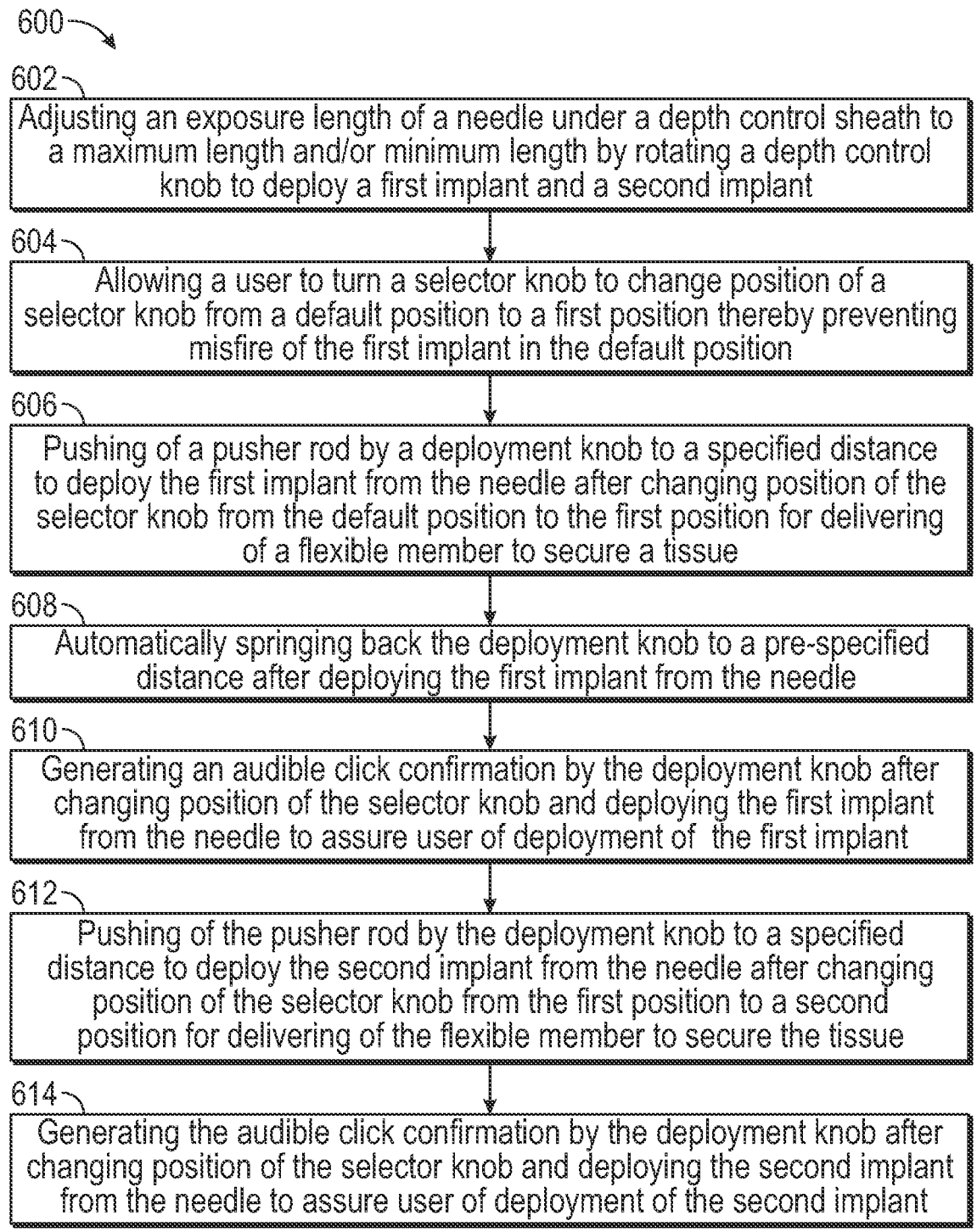
FIG. 6 is a flow diagram depicting a method of deploying implants to repair tissue using the tissue repair device, in accordance with one or more embodiments.

Referring to FIG. 6 is a flow diagram 600, depicting a method of deploying implants to repair tissue using the tissue repair device, in accordance with one or more embodiments. As an option, the method 600 is carried out in the context of the details of FIG. 1, FIG. 1A, FIG. 1B, FIG. 1C, FIG. 1D, FIG. 1F, FIG. 1G, FIG. 1H, FIG. 1I, FIG. 1J, FIG. 1K, FIG. 1L, FIG. 2A, FIG. 2B, FIG. 2C, FIG. 3A, FIG. 3B, FIG. 4A, FIG. 4B, FIG. 4C, FIG. 4D, FIG. 4E, FIG. 5A FIG. 5B, FIG. 5C, and FIG. 5D. However, the method 600 is carried out in any desired environment. Further, the aforementioned definitions are equally applied to the description below.

The method commences at step 602, adjusting the exposure length of the needle under the depth control sheath to the maximum length and/or the minimum length by rotating the depth control knob to deploy the first implant and the second implant. Thereafter, at step 604, allowing the user to turn the selector knob to change position of the selector knob from the default position to the first position thereby preventing misfire of the first implant in the default position. Thereafter, at step 606, pushing of the pusher rod by the deployment knob to a specified distance to deploy the first implant from the needle after changing position of the selector knob from the default position to the first position for delivering of the flexible member to secure the tissue. Thereafter, at step 608, automatically springing back the deployment knob to a pre-specified distance after deploying the first implant from the needle. Thereafter, at step 610, generating the audible click confirmation by the deployment knob after changing position of the selector knob and deploying the first implant from the needle to assure user of deployment of the first implant. Thereafter, at step 612, pushing of the pusher rod by the deployment knob to a specified distance to deploy the second implant from the needle after changing position of the selector knob from the first position to the second position for delivering of the flexible member to secure the tissue. Thereafter, at step 614, generating the audible click confirmation by the deployment knob after changing position of the selector knob and deploying the second implant from the needle to assure user of deployment of the second implant.

Although the present disclosure has been described in terms of certain preferred embodiments and illustrations thereof, other embodiments and modifications to preferred embodiments may be possible that are within the principles and spirit of the invention. The above descriptions and figures are therefore to be regarded as illustrative and not restrictive.

Thus the scope of the present disclosure is defined by the appended claims and includes both combinations and sub-combinations of the various features described hereinabove as well as variations and modifications thereof, which would occur to persons skilled in the art upon reading the foregoing description.

What is claimed is:

1. A tissue repair device to repair tissue by deploying implants, comprising:
   a handle; a depth control sheath coupled to said handle and a needle partially housed in said depth control sheath; whereby a series of implants comprising at least a first implant and a second implant are disposed entirely within said needle;
   a depth control knob configured to adjust an exposure length of said needle housed in said depth control sheath to an appropriate or desired length to deploy said first implant and said second implant or a last implant in the series of implants to secure with a tissue;
   a selector knob configured to allow a user to change from a default position to a first position, whereby said default position and said first position are indicated by a window positioned on said handle;
   a flexible member; and
   a deployment knob configured to push a pusher rod to deploy said first implant from said needle after changing said selector knob from said default position to said first position for delivering said flexible member to secure with said tissue, whereby said selector knob is configured to avoid misfire of said first implant in said default position, whereby said deployment knob configured to automatically spring back after deploying said first implant from said needle, said deployment knob configured to push said pusher rod to deploy said second implant from said needle after changing said selector knob from said first position to a second position for delivering of said flexible member to secure with said tissue, whereby said selector knob is configured to avoid misfire of said second implant in said first position.

2. The tissue repair device of claim 1, wherein said handle comprising a first pin fixed in said depth control knob and said first pin is locked inside a helical slot of a barrel cam.

3. The tissue repair device of claim 2, wherein said first pin is configured to force said barrel cam to slide in a backward direction when said depth control knob is rotated in a clockwise direction, thereby a length of said needle under said depth control sheath reaches to a maximum length.

4. The tissue repair device of claim 2, wherein said first pin is configured to force said barrel cam to slide in a forward direction when said depth control knob is rotated in a counter-clockwise direction, thereby said length of said needle under said depth control sheath reaches to a minimum length.

5. The tissue repair device of claim 2, wherein said handle comprising a spring loaded with a second pin, wherein said spring is trapped inside a stepped barrel groove.

6. The tissue repair device of claim 1, wherein said depth control sheath is attached to said depth control knob.

7. The tissue repair device of claim 1, wherein said first implant and said second implant are situated in a home position when said selector knob is positioned in said default position.

8. The tissue repair device of claim 1, wherein said selector knob is configured to be positioned in said first position after piercing of said needle to a first implant site, and said selector knob is configured to be positioned in said second position after piercing of said needle to a second implant site.

9. The tissue repair device of claim 8, wherein said needle is configured to be retracted by a user from said first implant site after deploying said first implant.

10. The tissue repair device of claim 8, wherein said needle is configured to be retracted by a user from said second implant site after deploying said second implant.

11. The tissue repair device of claim 1, wherein said flexible member couples to at least one of: said first implant; said second implant; and said last implant in said series of implants.

12. The tissue repair device of claim 11, wherein said flexible member comprising a first sliding knot and a second sliding knot located between at least two of: said first implant; said second implant; and last implant in said series of implants.

13. The tissue repair device of claim 12, wherein said flexible member comprising a pulling side which extends from said first sliding knot of a sliding side, and a length of said flexible member between at least two of: said first implant; said second implant; and said last implant in said series of implants is reduced upon pulling said pulling side in one direction.

14. The tissue repair device of claim 1, wherein said second implant or said last implant in said series of implants comprising a first notch configured to hold a second notch of said pusher rod.

15. The tissue repair device of claim 14, wherein said second notch of said pusher rod is configured to engage with said second implant to prevent slippage or accidental deployment of said second implant or said last implant in the series of implants while deploying said first or previous implant.

* * * * *